(12) United States Patent
Sako et al.

(10) Patent No.: US 9,406,123 B2
(45) Date of Patent: Aug. 2, 2016

(54) IMAGING CONTROL APPARATUS, STORAGE SYSTEM, AND STORAGE MEDIUM

(71) Applicant: Sony Corporation, Tokyo (JP)

(72) Inventors: Yoichiro Sako, Tokyo (JP); Akira Tange, Tokyo (JP); Takatoshi Nakamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/409,556

(22) PCT Filed: Apr. 5, 2013

(86) PCT No.: PCT/JP2013/060504
§ 371 (c)(1),
(2) Date: Dec. 19, 2014

(87) PCT Pub. No.: WO2014/002565
PCT Pub. Date: Jan. 3, 2014

(65) Prior Publication Data
US 2015/0254836 A1    Sep. 10, 2015

(30) Foreign Application Priority Data

Jun. 26, 2012  (JP) .................................. 2012-142619

(51) Int. Cl.
*G06K 9/00* (2006.01)
*G06T 7/00* (2006.01)
(Continued)

(52) U.S. Cl.
CPC ............. *G06T 7/0012* (2013.01); *A61B 1/0002* (2013.01); *A61B 1/00009* (2013.01); *A61B 1/04* (2013.01); *A61B 1/041* (2013.01); *G06F 17/3028* (2013.01); *G06K 9/46* (2013.01); *G06K 9/6201* (2013.01); *G06K 9/6253* (2013.01); *G06T 7/0016* (2013.01); *G06T 7/2053* (2013.01); *G06K 2009/4666* (2013.01); *G06K 2209/05* (2013.01); *G06T 2207/10068* (2013.01);
(Continued)

(58) Field of Classification Search
CPC ............... G06K 9/00; A61B 5/00; G06T 7/00
USPC .............. 382/128–134; 378/4, 8, 21–27, 901; 600/407, 410, 411, 425, 427, 300, 560
See application file for complete search history.

(56) References Cited

U.S. PATENT DOCUMENTS 6,951,536 B2 * 10/2005 Yokoi ................ A61B 1/00016
348/E5.026
7,912,265 B2 * 3/2011 Kemp .................. G06T 7/0012
128/922

(Continued)

FOREIGN PATENT DOCUMENTS

JP    2003-038425 A    2/2003
JP    2005-102851 A    4/2005
(Continued)

*Primary Examiner* — Abolfazl Tabatabai
(74) *Attorney, Agent, or Firm* — Chip Law Group (57) ABSTRACT

There is provided an imaging control apparatus including an imaging control section configured to control an imaging section to capture a predetermined area in a body cavity, a comparison section configured to compare a captured image captured by the imaging section with a reference image, and a storage control section configured to execute a control to store the captured image in response to a comparison result by the comparison section.

13 Claims, 9 Drawing Sheets

(51) Int. Cl.
*A61B 1/00* (2006.01)
*A61B 1/04* (2006.01)
*G06T 7/20* (2006.01)
*G06F 17/30* (2006.01)
*G06K 9/46* (2006.01)
*G06K 9/62* (2006.01)
*A61B 5/00* (2006.01)
*A61M 13/00* (2006.01)

(52) U.S. Cl.
CPC ............. *G06T 2207/30028* (2013.01); *G06T 2207/30092* (2013.01)

(56) References Cited

U.S. PATENT DOCUMENTS

| | | | |
|---|---|---|---|
| 7,993,263 B2 * | 8/2011 | Yokoi | A61B 1/00016 600/109 |
| 8,306,592 B2 * | 11/2012 | Takizawa | A61B 1/041 600/310 |
| 2003/0023150 A1 | 1/2003 | Yokoi et al. | |
| 2005/0148847 A1 | 7/2005 | Uchiyama et al. | |
| 2005/0158246 A1 | 7/2005 | Takizawa et al. | |
| 2005/0177069 A1 | 8/2005 | Takizawa et al. | |
| 2012/0062717 A1 | 3/2012 | Kinouchi et al. | |

FOREIGN PATENT DOCUMENTS

| | | |
|---|---|---|
| JP | 2005-103130 A | 4/2005 |
| JP | 2005-192879 A | 7/2005 |
| JP | 2005-204806 A | 8/2005 |
| JP | 2005-334331 A | 12/2005 |
| JP | 2007-014634 A | 1/2007 |
| JP | 2008-194334 A | 8/2008 |
| JP | 2010-046216 A | 3/2010 |
| JP | 2010-220794 A | 10/2010 |
| JP | 2012-010862 A | 1/2012 |
| JP | 4861540 A | 1/2012 |

\* cited by examiner

IMAGING CONTROL APPARATUS, STORAGE SYSTEM, AND STORAGE MEDIUM

TECHNICAL FIELD

The present disclosure relates to an imaging control apparatus, a storage system, and a storage medium.

BACKGROUND ART

In these days, encapsulated medical apparatuses administered into the body of a subject are known. As this kind of medical apparatuses, there are known an apparatus that takes a photograph of each part inside the body in a random manner, an apparatus that picks samples from the inside of the body, an apparatus that ejects medicine, etc.

For example, below Patent Literatures 1 and 2 propose an encapsulated endoscope that is provided with an engaging portion (a clip, an arm, or the like) for fixing itself on the tissue around the body cavity and stays in the body cavity to observe the development therein.

CITATION LIST

Patent Literature

Patent Literature 1: JP 2007-14634A
Patent Literature 2: JP 2005-204806A

SUMMARY OF INVENTION

Technical Problem

However, both of encapsulated endoscopes described above merely stays near a lesion area and observes the development, and a technology that pays attention to the change of a predetermined area in the body cavity is not disclosed.

Therefore, in the present disclosure, an imaging control apparatus, a storage system, and a storage medium capable of observing the change of the affected area in the body cavity are proposed.

Solution to Problem

According to the present disclosure, there is provided an imaging control apparatus including an imaging control section configured to control an imaging section to capture a predetermined area in a body cavity, a comparison section configured to compare a captured image captured by the imaging section with a reference image, and a storage control section configured to execute a control to store the captured image in response to a comparison result by the comparison section.

According to the present disclosure, there is provided a storage system including: an imaging control apparatus including an imaging control section configured to control an imaging section to capture a predetermined area in a body cavity, and a transmitter section configured to transmit a captured image captured by the imaging section; and a storage control apparatus including a receiver section configured to receive the captured image from the imaging control apparatus, a comparison section configured to compare the captured image received by the receiver section with a reference image, and a storage control section configured to execute a control to store the captured image in a storage section, in response to a comparison result by the comparison section.

According to the present disclosure, there is provided a storage medium storing a program for causing a computer to function as an imaging control section configured to control an imaging section to capture a predetermined area in a body cavity, a comparison section configured to compare a captured image captured by the imaging section with a reference image, and a storage control section configured to execute a control to store the captured image in response to a comparison result by the comparison section.

Advantageous Effects of Invention

As described above, according to the present disclosure, the change of the affected area in the body cavity is observed.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

Also, description will be made in the following order.
1. Overview of Observation System according to Embodiment of Present Disclosure
2. First Embodiment
2-1. Configuration
2-2. Operation Process
2-3. Exemplary Display
3. Second Embodiment
3-1. Configuration
3-2. Operation Process
4. Conclusion <<1. Overview of Observation System According to Embodiment of Present Disclosure>>

Figure 1:
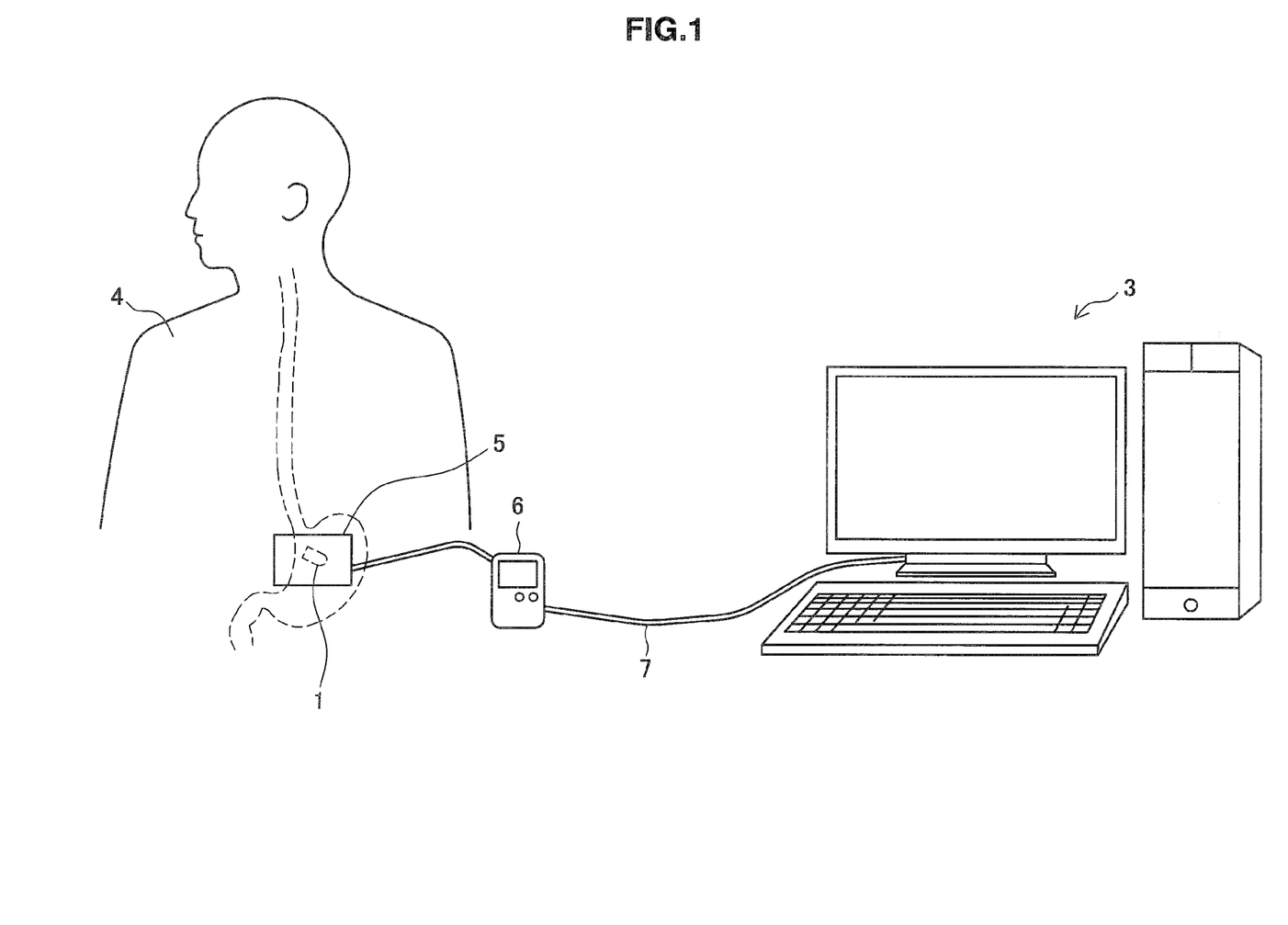
FIG. 1 is a diagram for describing an overview of an observation system according to an embodiment of the present disclosure.

First, description will be made of an overview of an observation system (a storage system) according to an embodiment of the present disclosure, with reference to FIG. 1. As illustrated in FIG. 1, the observation system according to the present embodiment includes an encapsulated medical apparatus 1 (hereinafter, also referred to as capsule 1) which is swallowed and taken into the body by a subject 4, as well as a control apparatus 3. Note that the capsule 1 illustrated in FIG. 1 has a communication function, and is capable of transmitting data to, and receiving data from, the external control apparatus 3.

For example, as illustrated in FIG. 1, when the subject 4 is provided with an antenna 5 attached on the body outside surface and a body external unit 6 in connection with the antenna 5, the data transmitted from the capsule 1 taken in the body cavity is received by the antenna 5, and is sent to the body external unit 6. Although in the example illustrated in FIG. 1 the antenna 5 is attached on the body outside surface near the stomach, the attachment location of the antenna 5 is not limited to near the stomach, and a plurality of antennae 5 may be attached on the body outside surface corresponding to respective areas such as esophagus and intestines, respectively. Alternatively, the antenna 5 may be designed capable of communicating with the capsule 1 regardless of the position of the capsule 1 in the body cavity, and be attached on the body outside surface of the subject 4 (or equipped on a shield shirt worn by the subject 4).

Then, the data sent from the antenna 5 to the body external unit 6 is transmitted from the body external unit 6 to the control apparatus 3. The body external unit 6 and the control apparatus 3 may have a removable wired connection through a communication cable 7 such as a USB cable as illustrated in FIG. 1, or may have a wireless connection. The body external unit 6 is provided with an operation buttons and a monitor on the front face. Also, the body external unit 6 may be a user terminal such as a smartphone and a PDA, for example.

Also, the capsule 1 can receive the data transmitted from the control apparatus 3 via the body external unit 6 and the antenna 5.

Here, as described above, in recent years, the encapsulated endoscope that takes a photograph of each part inside the body has been proposed. However, the technology that pays attention to the change of a predetermined area in the body cavity has not been disclosed.

Therefore, the observation system according to the embodiment of the present disclosure is created in view of the above circumstances. The observation system according to the embodiment of the present disclosure is capable of observing the change of the affected area in the body cavity.

According to the present embodiment, since a difference image between a current image and a past or future (predicting) image of a predetermined area in the body cavity is acquired, an abnormal area and a lesion are discovered in early stage, and a developing condition or a healing condition of disease is more accurately understood. Like this, the change of a predetermined area is extracted, so that the change of the disease state is observed promptly, which results in innovative progress in the medical technology.

In the following, detailed description will be made of the observation system according to the present disclosure, with a plurality of embodiments. Note that, in the example illustrated in FIG. 1, a personal computer (PC) is shown as one example of the control apparatus 3 according to the present embodiment, but the control apparatus according to the present disclosure is not limited thereto. For example, the control apparatus according to the present disclosure 3 may be a server, a smartphone, a PDA (Personal Digital Assistants), a notebook PC, a cellular phone, a portable music player, a portable video processing device, a portable game machine, or the like. Also, the encapsulated medical apparatus is used as one example of the imaging control apparatus according to the present disclosure.

<<2. First Embodiment<<
<2-1. Configuration>

The observation system according to the first embodiment includes the capsule 1 taken in the body cavity of the subject 4 and the control apparatus 3 as illustrated in FIG. 1. In the following, specific description will be made of each component of the capsule 1 and the control apparatus 3 included in the first embodiment.

(2-1-1. Configuration of Capsule)

Figure 2:
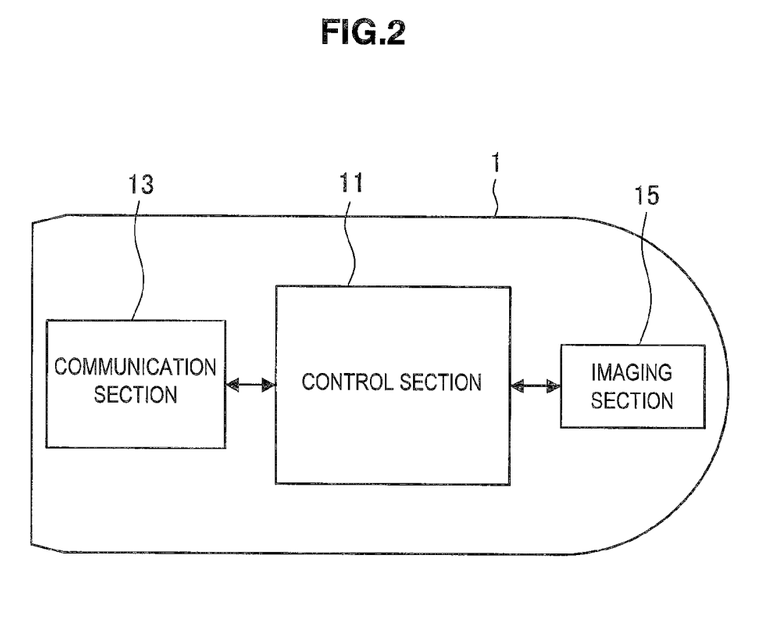
FIG. 2 is a block diagram illustrating a configuration of an encapsulated medical apparatus according to a first embodiment.

FIG. 2 is a block diagram illustrating the configuration of the capsule 1 according to the first embodiment. As illustrated in FIG. 2, the capsule 1 according to the present embodiment includes a control section 11, a communication section 13, and an imaging section 15.

(Control Section)

The control section 11 controls each component of the capsule 1. More specifically, the control section 11 serves as an imaging control section that controls the imaging section 15 to continually capture the inside of the body cavity while moving in the body cavity. Here, the control section 11 does not store the captured image captured by the imaging section 15, but executes a through image capturing control to transmit the captured images one after another in real time from the communication section 13 to the control apparatus 3. In the following, the image captured by the through image capturing control is referred to as a through image.

(Communication Section)

The communication section 13 is an interface to perform data communication with the control apparatus 3. More specifically, the communication section 13 according to the present embodiment continually transmits, to the control apparatus 3, the through image output from the imaging section 15.

(Imaging Section)

The imaging section 15 is realized by an illumination section such as a white LED, an imaging optical system including an imaging lens, and an imaging element (a CMOS imager, a CCD, or the like), and irradiates the inside of the body cavity with the white LED or the like, in order to capture an image.

In the above, specific description has been made of the configuration of the capsule 1 according to the present embodiment. Subsequently, description will be made of the configuration of the control apparatus 3 according to the first embodiment, with reference to FIG. 3.

(2-1-2. Configuration of Server)

Figure 3:
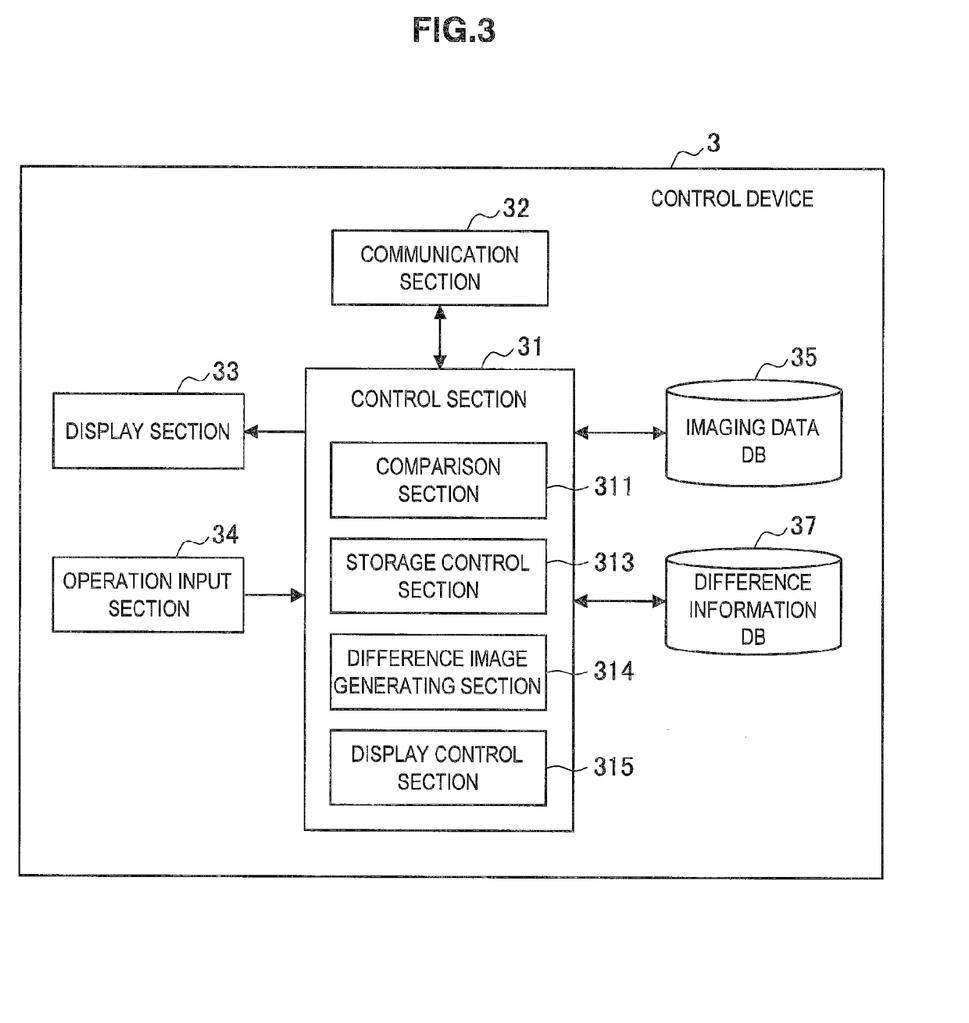
FIG. 3 is a block diagram illustrating a configuration of a control apparatus according to a first embodiment.

As illustrated in FIG. 3, the control apparatus 3 according to the present embodiment includes a control section 31, a communication section 32, a display section 33, an operation input section 34, an image database (DB) 35, and a difference information DB 37.

(Control Section)

The control section 31 has a function to control each component of the control apparatus 3. More specifically, the control section 31 according to the present embodiment may serve as a comparison section 311, a storage control section 313, a difference image generating section 314, and a display control section 315.

Comparison Section

The comparison section 311 is configured to compare the through image (the captured image) in the body cavity transmitted from the capsule 1 sequentially, with the reference image extracted from the image DB 35, and extract the difference (or the identical degree) between the both images as a result of the comparison, for example.

Also, in the present specification, the reference image is a past image or the future (predicting) image of a predetermined area. The future (predicting) image may be a deterioration predicting image generated on the basis of the prediction of the case where a predetermined area appearing in the past image is deteriorated, or a recovery predicting image generated on the basis of the prediction of the case where a predetermined area appearing in the past image is recovered (healed).

Also, the comparison section 311 may decide the reference image to be extracted from the image data DB 35 in accordance with the instruction by the user, or may extract a preset reference image.

Further, the comparison section 311 outputs the comparison result of the through image and the reference image to the storage control section 313.

Storage Control Section

The storage control section 313 executes a control to store, in the image data DB 35, the through image capturing the area same as the area appearing in the reference image, as a current image, on the basis of the comparison result by the comparison section 311. Also, the storage control section 313 may execute a control to store the through image in the image data DB 35, and the difference information included in the comparison result in the difference information DB 37.

For example, the storage control section 313 may store the through image substantially identical with the reference image in the image data DB 35.

Also, even if the area same as the area appearing in the reference image is captured, it is envisaged that the affected part of the through image is not identical with the reference image (for example, the past image) when the affected area is developed. Thereby, the storage control section 313 may execute a control to store a through image having a locally large difference (locally low identical degree) in the image data DB 35.

Also, the storage control section 313 may execute a control to store, in the image data DB 35, the through image having a smaller difference (a higher identical degree) as the comparison scope is made larger, on the basis of the result of comparison in which the comparison scope of the through image is made larger or smaller for comparison by the comparison section 311.

Also, the storage control section 313 may execute a control to store the through image, when the marker applied near a predetermined area appearing in the through image is identical with the marker appearing in the reference image.

Like this, the storage control section 313 stores, in the image data DB 35, as the current image, the through image capturing the area same as the reference image, from among the through images transmitted from the capsule 1 in real time.

Difference Image Generating Section

The difference image generating section 314 generates a difference image that images the difference between the captured image and the reference image, wherein the captured image is stored in the image data DB 35 by the aforementioned storage control section 313. More specifically, for example, the difference image generating section 314 generates the difference image on the basis of the difference information stored in the difference information DB 37, and the reference image and the captured image stored in the image data DB 35. The generating method of the difference image is not limited particularly, but an example of the difference image will be described later with reference to FIG. 7. Also, the generated difference image may be displayed on the display section 33 by the display control section 315 described next, or may be stored in the difference information DB 37.

Display Control Section

The display control section 315 controls the content (the display screen image) displayed on the display section 33. More specifically, for example, the display control section 315 may execute a control to display, on the display section 33, the difference image generated by the difference image generating section 314, the reference image, the current image, and others.

(Image Data DB)

The image data DB 35 is a storage section to store the reference images (the past image, the deterioration predicting image, the recovery predicting image, and the like), and the through image (the current image) in accordance with the control by the storage control section 313.

(Difference Information DB)

The difference information DB 37 is a storage section to store the difference information indicating the difference between the reference image and the through image, which is included in the comparison result by the comparison section 311. Also, the difference information DB 37 may store the difference image generated by the difference image generating section 314.

(Communication Section)

The communication section 32 is an interface for connecting with an external device and for transmitting and receiving data. More specifically, the communication section 32 according to the present embodiment receives the through image from the capsule 1.

(Display Section)

The display section 33 has a function to display screen images such as, an operation screen image and an observation result screen image in accordance with the control of the display control section 315. Note that the display section 33 may be realized by a LCD (Liquid Crystal Display), an OLED (Organic Light-Emitting Diode), a CRT (Cathode Ray Tube) or the like.

(Operation Input Section)

The operation input section 34 has a function to detect the operation by the user, and output to the control section 31 the input signal generated on the basis of the detected operation input. The operation input section 34 may be realized by a mouse, a keyboard, a touch panel, and the like.

In the above, detailed description has been made of each component of the capsule 1 and the control apparatus 3 included in the observation system according to the first embodiment. In the following, description will be made of the operation process of the observation system according to the present embodiment.

<2-2. Operation Process>

Figure 4:
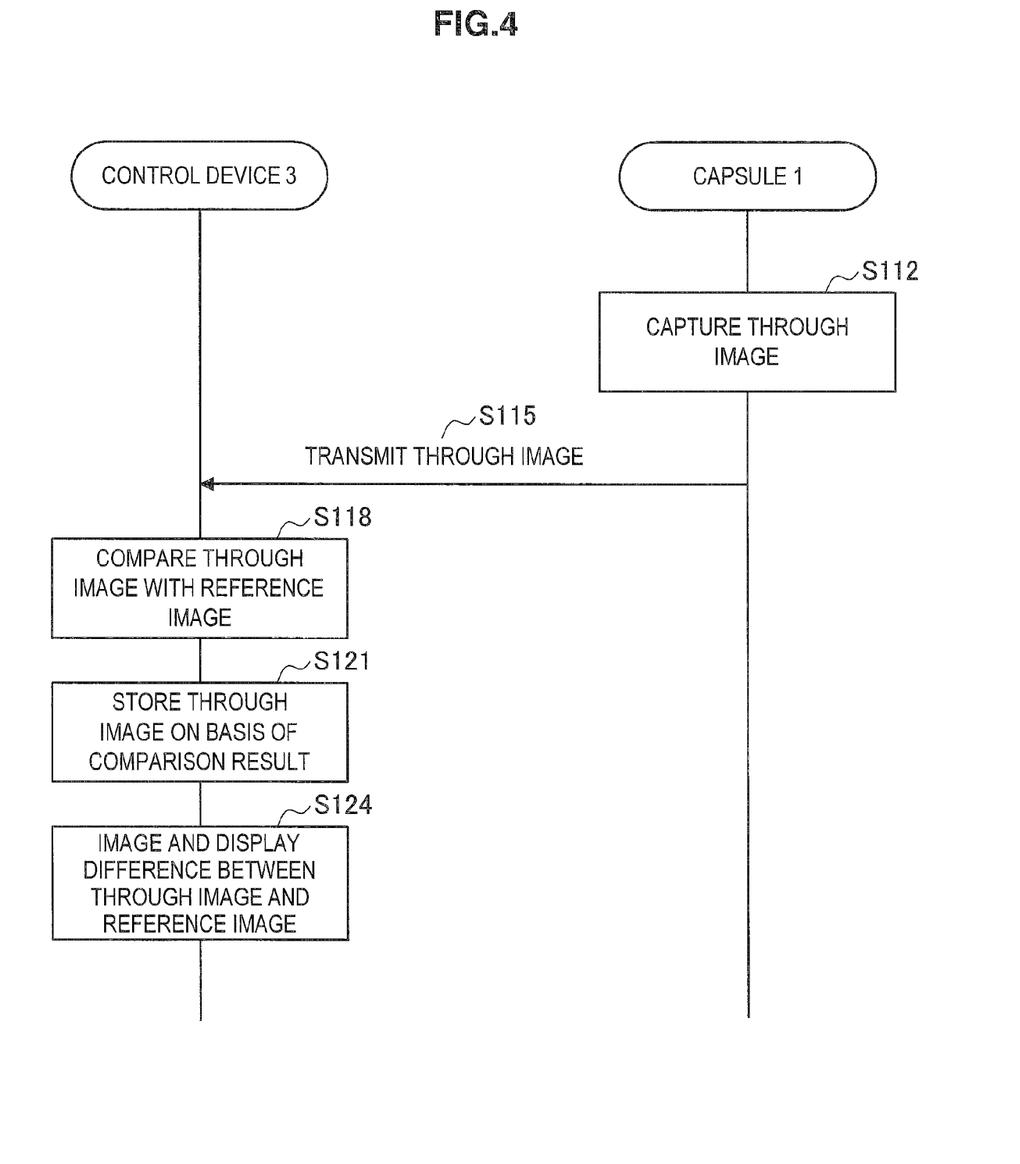
FIG. 4 is a flowchart illustrating an operation process of an observation system according to a first embodiment.

FIG. 4 is a flowchart illustrating the operation process of the observation system according to the first embodiment. As illustrated in FIG. 4, first, the capsule 1 captures the through image while moving in the body cavity of the subject 4 (step S112), and transmits one through image after another to the control apparatus 3 in real time (step S115).

Thereafter, the comparison section 311 of the control apparatus 3 compares the through image transmitted from the capsule 1 with the reference image (for example, the past image) extracted from the image data DB 35 (step S115).

Next, the storage control section 313 executes a control to store the through image in the image data DB 35 as the current image, on the basis of the comparison result by the comparison section 311 (step S121). As described above, the storage control section 313 executes a control to store the through image capturing the area same as the area appearing in the reference image.

Thereafter, the difference image generating section 314 generates the difference image that images the difference between the reference image and the through image, and controls the display control section 315 to display the difference image on the display section 33 (step S124).

<2-3. Exemplary Display>

In the above, detailed description has been made of the operation process of the observation system according to the first embodiment. Note that, in the observation system according to the present disclosure, the current image and the difference image may be displayed on the display section 33 of the control apparatus 3, for the purpose of confirming the observation result. In the following, with reference to FIGS. 5 to 7, description will be made of the observation result display screen image displayed on the display section 33.

(Operation Instruction Display)

Figure 5:
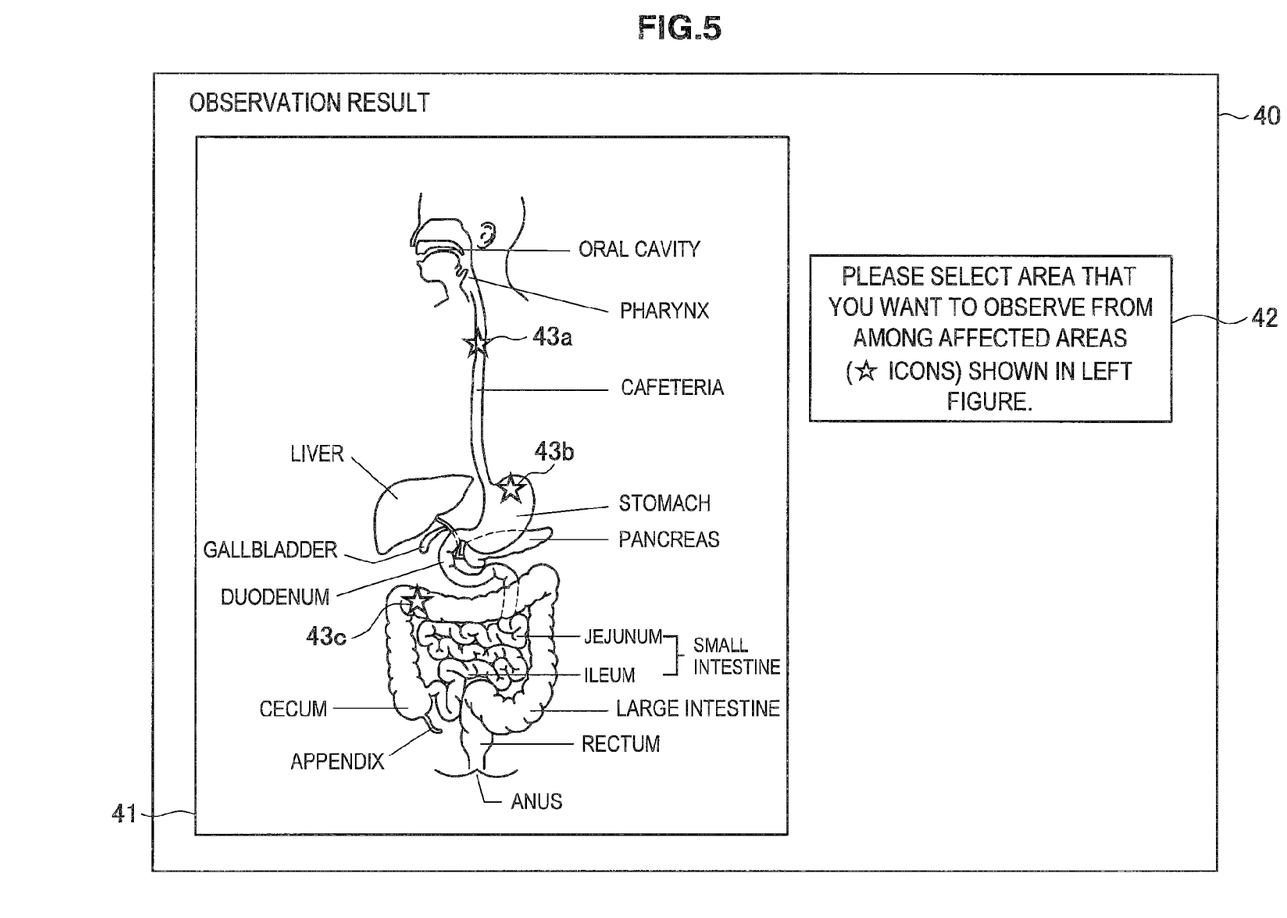
FIG. 5 is a diagram illustrating an example of an observation result display screen image.

FIG. 5 is a diagram illustrating an example of the observation result display screen image (hereinafter, referred to as the result screen image) according to the present embodiment. As illustrated in FIG. 5, the result screen image 40 includes an area screen image 41 presenting each body inside area and an operation instruction display 42.

As illustrated in FIG. 5, the area screen image 41 is the image in which the illustration of each area and the name are associate with each other. Also, on the area screen image 41, affected area icons 43a, 43b, 43c are displayed at positions corresponding to respective certain observed areas.

In the operation instruction display 42, an operation instruction such as "please select an area that you want to observe from among the affected areas shown in the left figure." is displayed for example.

(Menu Display)

Figure 6:
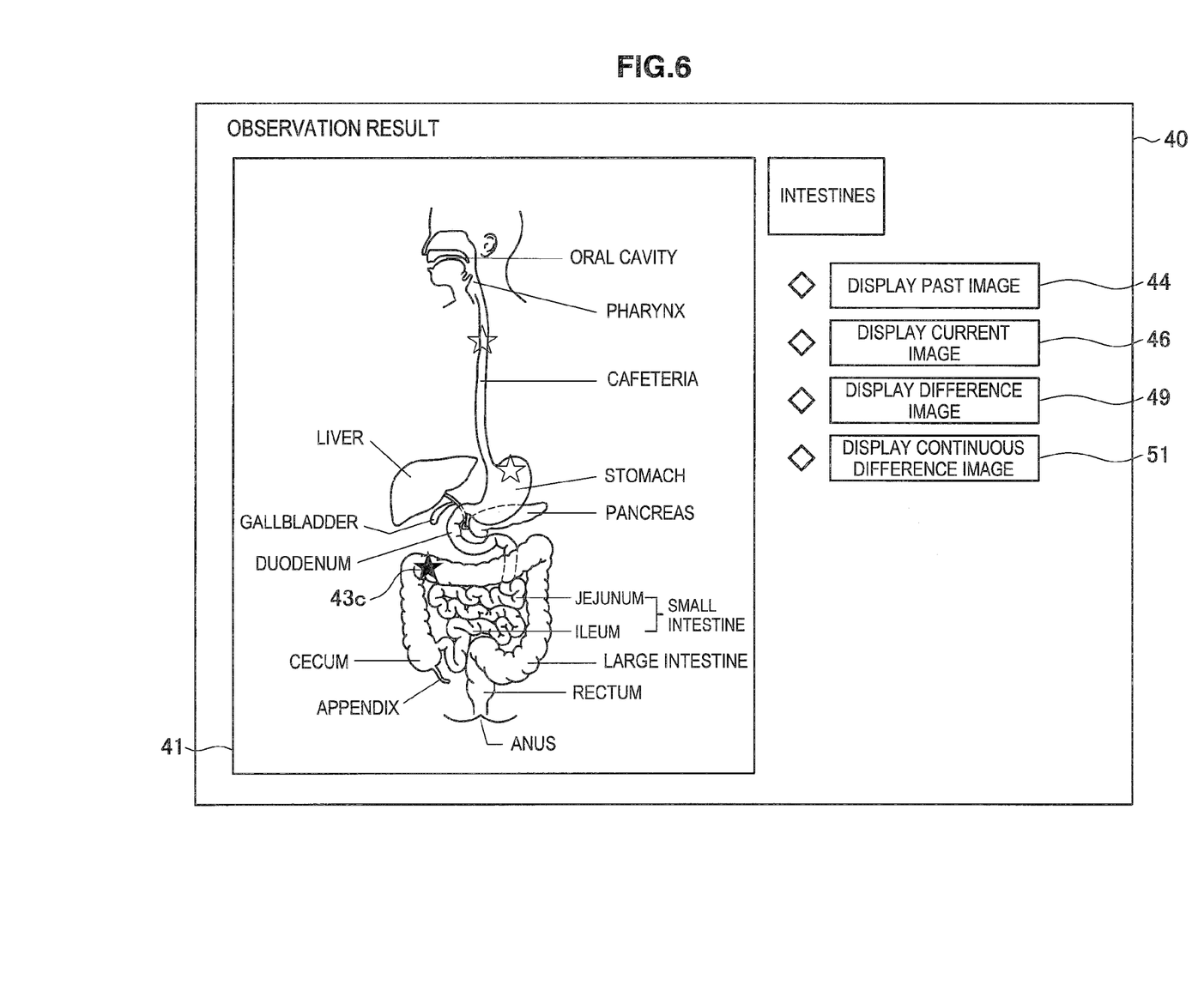
FIG. 6 is a diagram illustrating an example of a screen image displayed when an observation area is selected on the screen image illustrated in FIG. 5.

Next, description will be made of the case where the user selects one of the affected area icons displayed on the area screen image 41 in accordance with the operation instruction, with reference to FIG. 6. FIG. 6 is a diagram illustrating an exemplary screen image displayed after selecting the observation area in the result screen image 40 illustrated in FIG. 5.

For example, when the affected area icon 43c is selected, the menu buttons relevant to the observation result of the area corresponding to the affected area icon 43c is displayed. Specifically, as illustrated in FIG. 6, a past image display button 44, a current image display button 46, a difference image display button 49, and a continuous difference image display button 51 are displayed.

When the past image display button 44 is selected, the display control section 315 extracts the past image of a predetermined area corresponding to the affected area icon 43c from the image data DB 35, and displays it. Although the example using the past image is described here as one example of the reference image, the present embodiment is not limited to the example illustrated in FIG. 6. For example, when the reference image is the recovery predicting image or the deterioration predicting image, the display control section 315 may display the display button of each predicting image as the menu button.

Also, when the current image display button 46 is selected, the display control section 315 extracts the current image of a predetermined area corresponding to the affected area icon 43c from the image data DB 35, and display it.

(Difference Image Display)

Subsequently, description will be made of the case where the user selects the difference image display button 49. When the difference image display button 49 is selected, the display control section 315 displays the difference image generated by the difference image generating section 314 on the basis of the past image of a predetermined area corresponding to the affected area icon 43c, the current image, and the comparison result (the difference information). Here, an example of the difference image is illustrated in FIG. 7.

Figure 7:
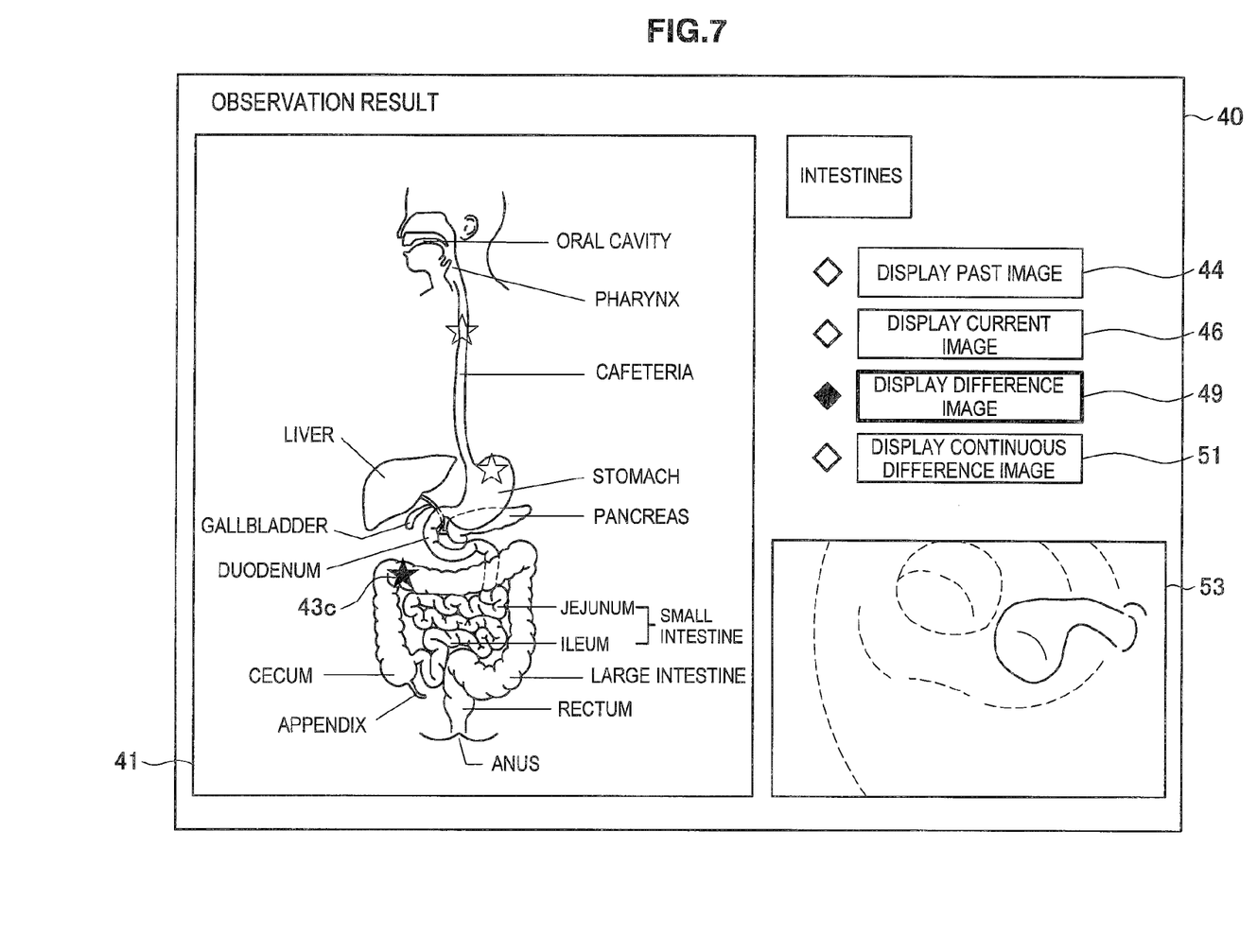
FIG. 7 is a diagram illustrating an exemplary display of a difference image.

In the difference image 53 illustrated in FIG. 7, a part (difference part) in the current image which is different from the past image is displayed with solid lines, and the identical parts are displayed with dashed lines, so that the change of the affected area (the difference between the past image and the current image) is clarified. Note that the expression method of the difference image is not limited thereto, but may be the method to display the difference part with a color different from the identical part, or may differentiate brightness, transparency, thickness of the identical part from the difference part, for example. Also, the identical parts may be colorless (undisplayed), while only the difference part is displayed with color.

Also, when the continuous difference image display button 51 is selected, the display control section 315 continuously displays the difference image of a predetermined area which is continually observed. The continuous display of the difference image may arrange and display a plurality of difference images in temporal sequence, or may display a plurality of difference images one after another in temporal sequence (moving image display), for example.

<<3. Second Embodiment>>

In the above, description has been made of the observation system according to the first embodiment of the present disclosure. Subsequently, description will be made of the observation system according to the second embodiment of the present disclosure.

As described with reference to FIG. 1 and FIG. 4, the observation system according to the first embodiment described above includes the capsule 1 and the control apparatus 3, and executes the comparison and storage control on the control apparatus 3 side. However, the observation system according to the present disclosure is not limited to the configuration according to the first embodiment, but may have the configuration in which the encapsulated medical apparatus executes the comparison and storage control, for example. In the following, detailed description will be made of the second embodiment in which the encapsulated medical apparatus executes the comparison and storage control as above, with reference to FIG. 8 to FIG. 9.

<3-1. Configuration of Capsule>

Figure 8:
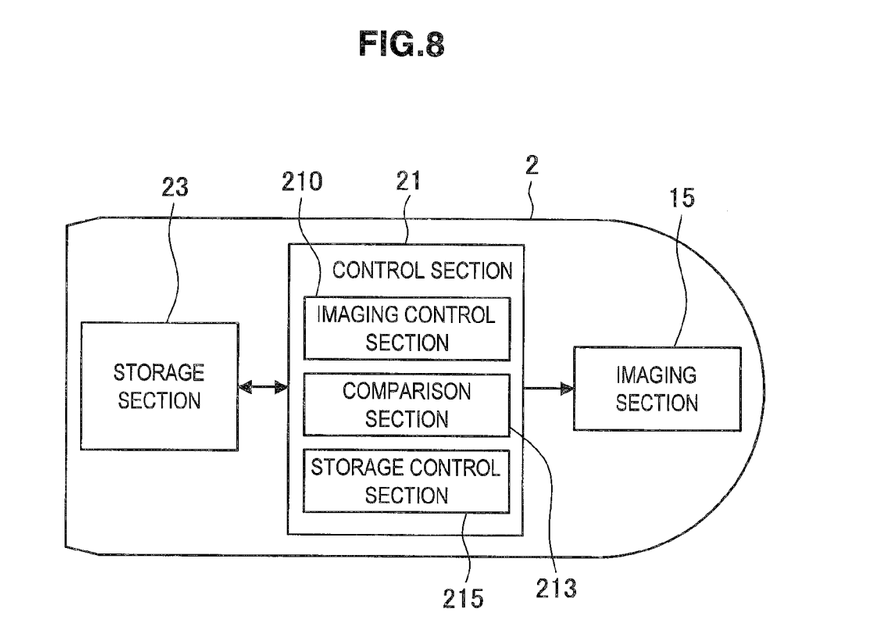
FIG. 8 is a block diagram illustrating a configuration of an encapsulated medical apparatus according to a second embodiment.

FIG. 8 is a block diagram illustrating the configuration of the encapsulated medical apparatus 2 according to the second embodiment. As illustrated in FIG. 8, the encapsulated medical apparatus 2 (hereinafter, referred to as the capsule 2) according to the present embodiment includes a control section 21, a storage section 23, and an imaging section 15. Note that the imaging section 15 is described in the above first embodiment, and will be omitted here.

(Control Section)

The control section 21 controls each component of the capsule 2. More specifically, the control section 21 serves as an imaging control section 210 configured to control the imaging section 15 to capture the inside of the body cavity, a comparison section 213, and a storage control section 215.

Imaging Control Section

The imaging control section 210 executes a control to continually capture a through image of the inside of the body cavity, while moving in the body cavity of the subject 4.

Comparison Section

The comparison section 213 may compare the through image (the captured image) captured by the imaging section 15 with the reference image stored in advance in the storage section 23, and extract the difference between the both images as a result of the comparison in the same way as the comparison section 311 according to the first embodiment described above, for example.

Also, when a plurality of reference images are stored in the storage section 23, the comparison section 213 may compare each reference image with the through image one after another.

Further, the comparison section 213 outputs the comparison result of the through image and the reference image to the storage control section 313.

Storage Control Section

The storage control section 215 executes a control to store the through image capturing the area same as the area appearing in the reference image, as the current image, in the storage section 23, on the basis of the comparison result by the comparison section 213. Also, the storage control section 215 may execute a control to store, in the storage section 23, the difference information included in the comparison result, in a related manner to the through image.

Since the specific storage control by the storage control section 215 is same as the storage control by the storage control section 313 according to the first embodiment described above, description thereof will be omitted here.

(Storage Section)

The storage section 23 may be realized by a ROM (Read Only Memory), a RAM (Random Access Memory) or the like, and may be a removable memory card. The storage section 23 according to the present embodiment is a storage section that stores the reference image (the past image, the deterioration predicting image, the recovery predicting image, and the like) described above, and the through image (the current image) in accordance with the control by the storage control section 215.

Also, the storage section 23 may store the difference information indicating the difference between the reference image and the through image, which is included in the comparison result by the comparison section 213.

In the above, description has been made of the configuration of the capsule 2 according to the second embodiment. Subsequently, description will be made of the operation process of the present embodiment, with reference to FIG. 9.

<3-2. Operation Process>

Figure 9:
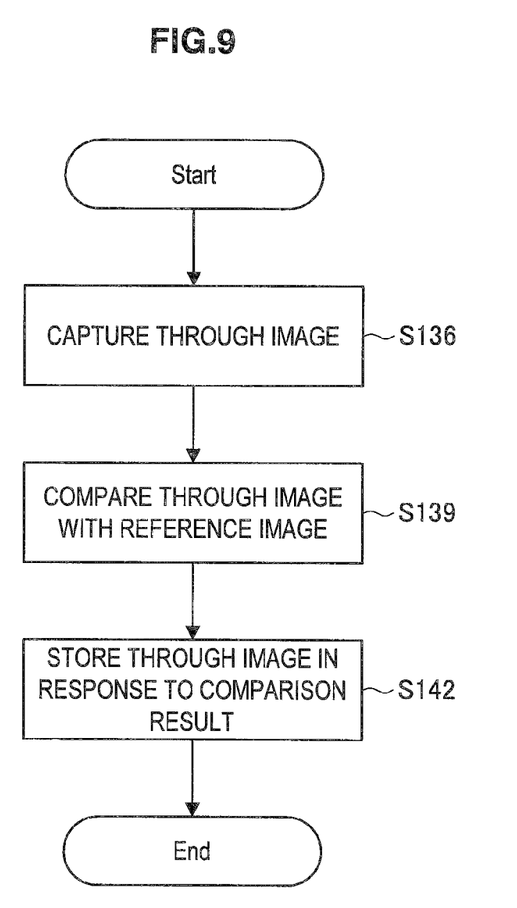
FIG. 9 is a flowchart illustrating an operation process according to a second embodiment.

FIG. 9 is a flowchart illustrating the operation process according to the second embodiment. As illustrated in FIG. 9, first, the imaging control section 210 of the capsule 2 taken in the body cavity executes a control to capture the through image of the inside of the body cavity by the imaging section 15 (step S136).

Next, the comparison section 213 compares the through image (the captured image) captured by the imaging section 15, with the reference image (for example, the past image) extracted from the storage section 23 (step S139).

Thereafter, the storage control section 215 executes a control to store the through image in the storage section 23 as the current image, on the basis of the comparison result by the comparison section 213 (step S142). As described above, the storage control section 215 executes a control to store the through image capturing the area same as the area appearing in the reference image.

In the above, detailed description has been made of the operation process of the observation system according to the present embodiment. Note that the capsule 2 described above moves in the body cavity, and is excreted from the subject 4 naturally, and thereafter is collected by the user such as the subject 4 and medical staff, and the current image, the difference information, and others stored in the storage section 23 are taken out. The current image, the difference information, and others taken from the capsule 2 are used when generating the difference image described above, or used when displaying the observation result display screen image described in above "2-3. Exemplary Display".

<<4. Conclusion>>

As described above, in the observation system according to the embodiment of the present disclosure, a control to store the through image capturing the area same as the reference image (the affected area) is executed to make the change of the affected area observable.

Specifically, the through image is stored on the basis of the comparison result (the difference) of the reference image and the through image, in such a manner that the through image having the capturing scope identical with the capturing scope of the reference image is stored (taken a photograph) as the current image (the captured image), from among the through images capturing the inside of the body cavity in real time. In this case, since the difference between the reference image and the current image is the changing part of the affected area, the user such as the subject 4 and medical staff can observe the change of the affected area, by displaying the difference image that images the difference, for example.

Also, by displaying a plurality of difference images in temporal sequence, the user can monitor the development and others of the affected area after the operation.

Also, by displaying, the difference image of the current image relative to the reference image which is either the recovery predicting image that predicts the recovery of the affected area or the deterioration predicting image that predicts the deterioration of the affected area, whether the affected area is going toward recovery or deterioration can be confirmed. Thereby, the user can continue the treatment commensurate with the healing degree of the early stage of the affected area, and the developing condition of the disease.

The preferred embodiments of the present invention have been described above with reference to the accompanying drawings, whilst the present invention is not limited to the above examples, of course. A person skilled in the art may find various alterations and modifications within the scope of the appended claims, and it should be understood that they will naturally come under the technical scope of the present invention.

For example, the capsules 1, 2 according to each embodiment described above may control the capturing scope by the imaging section 15 in such a manner that the reference image and the capturing scope are identical with each other (adjust the position to each other) on the basis of the comparison result of the reference image and the through image.

Also, in the above first embodiment, the capsule 1 may receive the reference image from the control apparatus 3 or have the reference image in advance, to compare the reference image and the through image. In this case, the control section 31 of the capsule 1 may transmit the through image capturing the area same as the area appearing in the reference image to the control apparatus 3, or may transmit the difference information indicating the difference between the through image and the reference image to the control apparatus 3. Thereby, the transmitted data amount is reduced, as compared to the first embodiment in which the through image is continually transmitted to the control apparatus 3 in real time.

Also, the image stored as the current image by the storage control section in the above each embodiment is treated as the past image when the next current image of the same area is acquired.

Also, the observation system according to the present embodiment may warn the non-smooth recovery in the observation result display screen image, when the current image is compared with each of the deterioration predicting image and the recovery predicting image, resulting in the current image closer to the deterioration predicting image than to the recovery predicting image.

Also, although the image data DB 35 and the difference information DB 37 according to the first embodiment are provided in the control apparatus 3, the present disclosure is not limited thereto, and the image data DB and the difference information DB may be provided on the network in connection with the control apparatus 3 for example.

Further, in the above first embodiment, when the comparison by the comparison section 311 results in the difference between the current image capturing a predetermined area and the reference image being equal to or greater than a predetermined threshold value, the control section 31 of the control apparatus 3 (the storage control apparatus) may serve as a notification section that provides a warning notification to notify the user such as the subject and medical staff of an abnormal change discovered. The notification section can notify the user of the abnormal change (a lesion area) by displaying the warning display on the display section 33, for example.

Also, in the above second embodiment, when the comparison by the comparison section 213 results in the difference between the current image capturing a predetermined area and the reference image being equal to or greater than a predetermined threshold value, the control section 21 of the capsule 2 (the imaging control apparatus) may serve as a notification section that provides a warning notification to notify the user (outside) such as the subject and medical staff of an abnormal change discovered. The notification section is able to notify the user of an abnormal change (a lesion area), by sending a warning notification to the external device via the communication section (not illustrated in the drawings) of the capsule 2, for example.

Additionally, the present technology may also be configured as below.

(1)
 An imaging control apparatus including:
 an imaging control section configured to control an imaging section to capture a predetermined area in a body cavity,
 a comparison section configured to compare a captured image captured by the imaging section with a reference image, and
 a storage control section configured to execute a control to store the captured image in response to a comparison result by the comparison section.

(2)
 The imaging control apparatus according to (1), wherein
 the imaging control apparatus is an encapsulated medical apparatus.

(3)
 The imaging control apparatus according to (1) or (2), wherein
 the storage control section executes a control to store the captured image having a locally large difference from the reference image, on the basis of the comparison result.

(4)
 The imaging control apparatus according to any one of (1) to (3), wherein
 the storage control section executes a control to store the captured image having a smaller difference as the comparison scope is larger, on the basis of a comparison result of a case in which a comparison scope of the captured image is made larger or smaller for comparison by the comparison section.

(5)
 The imaging control apparatus according to any one of (1) to (4), wherein
 the storage control section executes a control to store the captured image when a marker appearing in the captured image and applied near a predetermined area is identical with a marker appearing in the reference image.

(6)
 The imaging control apparatus according to any one of (1) to (5), wherein
 the reference image is a past image of the predetermined area, or a predicting image generated by predicting change of the predetermined area.

(7)
 The imaging control apparatus according to (6), wherein
 the predicting image is a recovery predicting image generated by processing a captured image of the predetermined area on the basis of a prediction of a situation in which the predetermined area is recovered, or a deterioration predicting image generated by processing a captured image of the predetermined area on the basis of a prediction of a situation in which the predetermined area is deteriorated.

(8)
 The imaging control apparatus according to any one of (1) to (7), wherein
 the imaging control apparatus further includes a notification section configured to provide a warning notification to an outside, when comparison by the comparison section results in a difference between the captured image and the reference image being equal to or greater than a predetermined threshold value.

(9)
 A storage system including:
 an imaging control apparatus including
   an imaging control section configured to control an imaging section to capture a predetermined area in a body cavity, and
   a transmitter section configured to transmit a captured image captured by the imaging section; and
 a storage control apparatus including
   a receiver section configured to receive the captured image from the imaging control apparatus,
   a comparison section configured to compare the captured image received by the receiver section with a reference image, and
   a storage control section configured to execute a control to store the captured image in a storage section, in response to a comparison result by the comparison section.

(10)
 The storage system according to (9), wherein
 the storage control apparatus further includes a display control section configured to execute a control to display the comparison result by the comparison section.

(11)
 The storage system according to (10), wherein
 the comparison section outputs a difference between the captured image and the reference image as the comparison result, and
 the display control section executes a control to display a difference image in which the difference is imaged.

(12)
 The storage system according to (11), wherein
 the storage control apparatus further includes
 a notification section configured to provide a warning notification, when comparison by the comparison section results in a difference between the captured image and the reference image being equal to or greater than a predetermined threshold value.

(13) A storage medium storing a program for causing a computer to function as an imaging control section configured to control an imaging section to capture a predetermined area in a body cavity, a comparison section configured to compare a captured image captured by the imaging section with a reference image, and a storage control section configured to execute a control to store the captured image in response to a comparison result by the comparison section.

REFERENCE SIGNS LIST 1, 2 encapsulated medical apparatus
3 control apparatus
4 subject
5 antenna
6 body external unit
7 communication cable
11 control section
13 communication section
15 imaging section
21 control section
210 imaging control section
213 comparison section
215 storage control section
23 storage section
31 control section
311 comparison section
313 storage control section
314 difference image generating section
315 display control section
32 communication section
33 display section
34 operation input section
35 image data DB
37 difference information DB

The invention claimed is:

1. An imaging control apparatus comprising:
one or more processors configured to:
control an imaging section to capture a predetermined area in a body cavity,
compare a captured image captured by the imaging section with a reference image, and
execute a control to store the captured image in response to a comparison result,
wherein a warning notification is provided to an outside in case the comparison result indicates that a difference between the captured image and the reference image is equal to or greater than a predetermined threshold value.

2. The imaging control apparatus according to claim 1, wherein
the imaging control apparatus is an encapsulated medical apparatus.

3. The imaging control apparatus according to claim 1, wherein
the one or more processors are configured to execute a control to store the captured image having a locally large difference from the reference image, on the basis of the comparison result.

4. The imaging control apparatus according to claim 1, wherein
the one or more processors are configured to execute a control to store the captured image having a smaller difference as a comparison scope is made larger, on the basis of the comparison result of a case in which the comparison scope of the captured image is made larger or smaller for the comparison.

5. The imaging control apparatus according to claim 1, wherein
the one or more processors are configured to execute a control to store the captured image when a marker appearing in the captured image and applied near the predetermined area is identical with a marker appearing in the reference image.

6. The imaging control apparatus according to claim 1, wherein
the reference image is a past image of the predetermined area, or a predicting image generated by predicting change of the predetermined area.

7. The imaging control apparatus according to claim 6, wherein
the predicting image is a recovery predicting image generated by processing a captured image of the predetermined area on the basis of a prediction of a situation in which the predetermined area is recovered, or a deterioration predicting image generated by processing a captured image of the predetermined area on the basis of a prediction of a situation in which the predetermined area is deteriorated.

8. A storage system comprising:
first one or more processors configured to:
control an imaging section to capture a predetermined area in a body cavity, and
transmit a captured image captured by the imaging section; and
second one or more processors configured to:
receive the captured image from the first one or more processors,
compare the received captured image with a reference image, and
execute a control to store the captured image in a storage section, in response to a comparison result,
wherein a warning notification is provided to an outside in case the comparison result indicates that a difference between the captured image and the reference image is equal to or greater than a predetermined threshold value.

9. The storage system according to claim 8, wherein
the one or more processors are further configured to execute a control to display the comparison result.

10. The storage system according to claim 9, wherein
the one or more processors are further configured to:
output a difference between the captured image and the reference image as the comparison result, and
execute a control to display a difference image in which the difference is imaged.

11. A non-transitory computer readable storage medium having stored thereon, a set of computer executable instructions, for causing a computer to perform steps comprising:
controlling an imaging section to capture a predetermined area in a body cavity,
comparing a captured image captured by the imaging section with a reference image, and
executing a control to store the captured image in response to a comparison result,
wherein a warning notification is provided to an outside in case the comparison result indicates that a difference between the captured image and the reference image is equal to or greater than a predetermined threshold value.

12. An imaging control apparatus comprising:
one or more processors configured to:
- control an imaging section to capture a predetermined area in a body cavity,
- compare a captured image captured by the imaging section with a reference image, and
- execute a control to store the captured image in response to a comparison result,
- wherein the one or more processors are configured to execute a control to store the captured image having a smaller difference as a comparison scope is made larger, on the basis of the comparison result of a case in which the comparison scope of the captured image is made larger or smaller for the comparison.

13. An imaging control apparatus comprising:
one or more processors configured to:
- control an imaging section to capture a predetermined area in a body cavity,
- compare a captured image captured by the imaging section with a reference image, and
- execute a control to store the captured image in response to a comparison result,
- wherein the one or more processors are configured to execute a control to store the captured image in case a marker appearing in the captured image and applied near the predetermined area is identical with a marker appearing in the reference image.

* * * * *